United States Patent [19]

Retnakaran

[11] 4,427,700

[45] Jan. 24, 1984

[54] REPELLENT FOR BLACK FLY

[75] Inventor: Arthur Retnakaran, Sault Ste. Marie, Canada

[73] Assignee: Canadian Patents & Dev. Ltd., Ottawa, Canada

[21] Appl. No.: 327,250

[22] Filed: Dec. 3, 1981

Related U.S. Application Data

[63] Continuation of Ser. No. 147,964, May 8, 1980, abandoned.

[30] Foreign Application Priority Data

Jul. 18, 1979 [CA] Canada ................................... 332067

[51] Int. Cl.³ ...................... A01N 37/18; A01N 35/00
[52] U.S. Cl. .................................... 424/324; 424/333; 424/DIG. 10
[58] Field of Search ................ 424/324, 333, DIG. 10

[56] References Cited

PUBLICATIONS

Khan et al., "Mosquito News", vol. 35 (2), 223–225, (1975).
King, Chemicals Evaluated as Insecticides and Repellants at Orlando, Fla., (1954), pp. 13–17, 326, 327, 337, 386 & 394.

*Primary Examiner*—Douglas W. Robinson
*Attorney, Agent, or Firm*—Alan A. Thomson

[57] ABSTRACT

A significant enhancement of repellency toward the black fly (*Simulium venustum* Say, and *Prosimulium hirtipes* Fries) of N,N-diethyl-m-toluamide has been obtained by the addition, or conjunctive application of, vanillin, with the vanillin being present in minor proportion relative to the toluamide. A surprising decrease in black fly landings on the skin and bitings, was observed when the combination was used, compared to the toluamide alone.

8 Claims, No Drawings

REPELLENT FOR BLACK FLY

This application is a continuation of Ser. No. 147,964 filed May 8, 1980 now abandoned.

This invention deals with an insect repellent particularly for use against black flies of the type *Simulium venustum* Say and *Prosimulium hirtipes* Fries. A binary mixture has been found to show a surprising enhancement of repellent effect toward, and substantially complete elimination of the biting response on landing of, black flies.

Adult black flies, notably *Simulium venustum* Say and *Prosimulium hirtipes* Fries, are well known for their blood feeding habit (Twinn and Peterson, Can. Dept. Agr., Publ. 940, 1955). Although not implicated as vectors of human diseases in North America, their nuisance value is beyond argument. They are a considerable hazard for those who must work regularly in the forest, and decrease the efficiency of such personnel. The most common method for alleviating this problem is the use of insect repellents. One of the factors that complicates the testing of candidate repellent compounds for black flies is their feeding behavior which has been grouped into four phases: (i) activation; (ii) orientation and location of host; (iii) landing and probing; (iv) and finally, biting and ingestion of blood (Sutcliffe and McIver, Experientia, 31: 694-695, 1975). Unless they have completed the first three phases, they do not "bite". Under laboratory conditions they do not perform the first three steps. For this reason, it is extremely difficult to conduct meaningful repellency tests in the laboratory and very little controlled testing has been reported.

One common repellent ingredient in some commercial insect repellent compositions is N,N-diethyl-m-toluamide (DEET). This repellent is primarily used against mosquitos for which it is quite effective, but is only mediocre in efficacy against black flies. It would be very desirable to enhance the effect of DEET against black flies (without decreasing the effect against mosquitos).

Vanillin (4-hydroxy-3-methoxybenzaldehyde) has been tested with seven mosquito repellent chemicals in efforts to increase the protection time against mosquitos using human subjects (See A. A. Khan et al, "Mosquito News", Vol. 35, No. 2 pp. 223-225, June 1975). Vanillin was tested with DEET by Khan et al at weight ratios of 1:1, 2:1, and 3:1, respectively. For the two higher wt. ratios, the protection time against mosquitos was increased from about 5 to about 12-14 hrs. (there was a lesser increase at the 1:1 wt. ratio). These tests gave no indication that the degree of protection of DEET against mosquitos was enhanced at any concentration.

In accordance with the present invention, I have now found that minor proportions of vanillin with DEET cause a reduction in black fly landings on the skin and substantially complete elimination of bites by the few black flies that do land, compared to DEET alone. Vanillin by itself was not significantly effective in reducing the incidence of biting by black flies (compared to no repellent): fewer flies landed but most of those that did land showed a biting response.

This invention provides an insect repellent composition particularly for black flies, comprising: (a) N,N-diethyl-m-toluamide, and (b) vanillin, the vanillin being present in minor proportion by weight relative to toluamide (a). The invention includes a method of enhancing the repellency of N,N-diethyl-m-toluamide toward black flies and substantially eliminating their biting response on landing, comprising applying vanillin to the surface to be protected in conjunction with said toluamide, the vanillin being applied in an effective minor proportion by weight relative to said toluamide. The vanillin may be applied separately from the DEET instead of as a mixture.

The preferred proportion by weight of vanillin to toluamide is within the approximate range of 1:5 to 1:2.

The compositions are usually applied in the form of a solution in a solvent suitable for application to the skin (and preferably also to clothing). Solvents which may be used include lower alkanols such as methanol, ethanol, propanol (including isopropanol) and mixtures thereof, and water-lower alkanol mixtures (the water being in minor proportion by volume). Ethanol itself or with up to about 30% by vol. water is usually preferred. The concentration of solution applied may range from about 10% wt./vol. up to saturation, with about 20-60% usually being most suitable. The concentration of vanillin in solution is usually within about 5 to 20% wt./vol.

The solutions are usually applied directly by hand to the skin or clothing area to be protected but can be sprayed on mechanically or using a propellent under pressure. Alternatively, the active ingredients can be formulated into a paste or spreadable solid and applied from a tube or jar, or as a "stick" (like a lipstick). The vanillin can also be provided as a concentrate for addition to a commercial DEET preparation before application.

The following examples are illustrative.

EXAMPLE 1

Forestry workers from the Canadian Forestry Service have tested the effects of vanillin-DEET mixtures under field conditions in Northern Ontario. Vanillin was dissolved in ethanol at a concentration of 5 g. vanillin per ml. and this concentrate then added to a commercial repellent containing 47.5% DEET to give a final solution concentration of about 10% vanillin and about 50% DEET. This combined formulation was tested by 25 subjects over extended periods under various conditions (in comparison with the commercial 48% DEET repellent). The comparison was based on both landings and bites. Twenty three out of the 25 subjects reported that the test mixture was a more effective repellent.

EXAMPLE 2

Further comparative tests were conducted in the spring of 1978 near Hearst, Ontario. A solution containing 10% vanillin and 20% DEET was tested against, as control, a 20% solution of DEET. Five human subjects, with protective clothing except for both arms, sat near a stream for 3 hours and continuously recorded black fly landings and bites. One ml. of the vanillin-DEET mixture was applied on one arm and one ml. of the control DEET solution on the other arm of each subject. The experiment was repeated three additional times with similar results. Results are summarized in the Table. The addition of minor amounts of vanillin reduced the landing response about 3 fold (significant at the 5% level in a paired t - test) and fewer bites were recorded (biting was substantially eliminated). Vanillin by itself reduced landings (but less than DEET alone), however, most flies that landed proceeded to bite. No adverse skin reactions were encountered.

TABLE

Effect of DEET (20%) With and Without Vanillin (10%) On Black Fly Landing and Biting Over a 3 hr Period

| Subject | DEET Landing | DEET Biting | Vanillin + DEET Landing | Vanillin + DEET Biting | Relative landing rate $\left(\dfrac{\text{DEET}}{\text{Vanillin + DEET}}\right)$ |
|---|---|---|---|---|---|
| 1 | 28 | 0 | 11 | 0 | 2.5 |
| 2 | 38 | 0 | 12 | 0 | 3.1 |
| 3 | 42 | 3 | 7 | 0 | 6.0 |
| 4 | 4 | 0 | 0 | 0 | — |
| 5 | 9 | 1 | 4 | 0 | 2.2 |
| Total | 121 | 4 | 34 | 0 | 13.8 |
| $\bar{x}$ | 24.2 | 0.8 | 6.8 | 0 | 3.4 |

(calculated t = 2.91, 5% t = 2.77, d.f. = 4)

I claim:

1. An insect repellent composition particularly for black flies, comprising:
   (a) N,N-diethyl-m-toluamide and
   (b) vanillin,
   the vanillin being present in proportion by weight relative to toluamide (a) ranging from about 1:5 up to about 1:2.

2. The repellent composition of claim 1 wherein the proportion by wt. of vanillin to toluamide (a) is approximately 1:5.

3. The repellent composition of claim 1 wherein the proportion by wt. of vanillin to toluamide (a) is about 1:2.

4. The repellent composition of claim 1 wherein solvent is present forming a solution of about 20 to about 60% by wt. concentration.

5. The repellent composition of claim 1 including ethanol as solvent.

6. A method of enhancing the repellency of N,N-diethyl-m-toluamide toward black flies and substantially eliminating their biting response on landing, comprising applying vanillin to the surface to be protected in admixture with said toluamide or in any sequence therewith, the vanillin being applied in proportions by weight relative to said toluamide ranging from about 1:5 up to about 1:2.

7. The method of claim 6 wherein the proportion by wt. vanillin to toluamide is approximately 1:5.

8. The method of claim 6 wherein the vanillin is applied as a solution of concentration from about 5% to about 20% vanillin wt./vol.

* * * * *